United States Patent
Ueno et al.

(10) Patent No.: US 8,303,487 B2
(45) Date of Patent: Nov. 6, 2012

(54) POWER DRIVEN BENDING ENDOSCOPE DEVICE WITH DETACHABLE INSERTION PORTION

(75) Inventors: Haruhiko Ueno, Akiruno (JP); Tatsuya Ishizuka, Hachioji (JP); Yuichi Ikeda, Tama (JP); Tatsuya Furukawa, Hachioji (JP); Yutaka Masaki, Mitaka (JP); Masanobu Koitabashi, Hachioji (JP); Noriaki Kanazawa, Musashino (JP)

(73) Assignee: Olympus Corporation, Tokyo (JP)

( * ) Notice: Subject to any disclaimer, the term of this patent is extended or adjusted under 35 U.S.C. 154(b) by 1308 days.

(21) Appl. No.: 11/809,084

(22) Filed: May 31, 2007

(65) Prior Publication Data

US 2007/0232856 A1 Oct. 4, 2007

Related U.S. Application Data

(63) Continuation of application No. PCT/JP2005/022199, filed on Dec. 2, 2005.

(30) Foreign Application Priority Data

Dec. 3, 2004 (JP) .................................. 2004-351803
Dec. 13, 2004 (JP) .................................. 2004-360320

(51) Int. Cl.
*A61B 1/00* (2006.01)
(52) U.S. Cl. ...................................... 600/146; 600/152
(58) Field of Classification Search .................. 600/145, 600/146, 147, 150, 152
See application file for complete search history.

(56) References Cited

U.S. PATENT DOCUMENTS

| | | | |
|---|---|---|---|
| 5,469,840 A | 11/1995 | Tanii et al. | |
| 6,371,907 B1 * | 4/2002 | Hasegawa et al. | 600/146 |
| 6,932,761 B2 * | 8/2005 | Maeda et al. | 600/152 |
| 7,722,532 B2 * | 5/2010 | Ikeda et al. | 600/146 |
| 2004/0054258 A1 | 3/2004 | Maeda et al. | |
| 2004/0073083 A1 | 4/2004 | Ikeda et al. | |
| 2005/0054899 A1 * | 3/2005 | Miyake | 600/152 |

FOREIGN PATENT DOCUMENTS

| | | |
|---|---|---|
| JP | 06-105800 | 4/1994 |
| JP | 06-114001 | 4/1994 |
| JP | 06-217928 | 8/1994 |
| JP | 06-269398 | 9/1994 |
| JP | 10-234651 | 9/1998 |
| JP | 2003-159214 | 6/2003 |
| JP | 2003-245246 | 9/2003 |
| JP | 2003-275168 | 9/2003 |
| JP | 2004-337251 | 12/2004 |

OTHER PUBLICATIONS

Extended Supplementary European Search Report dated Aug. 17, 2011.

* cited by examiner

*Primary Examiner* — Philip R Smith
(74) *Attorney, Agent, or Firm* — Scully, Scott, Murphy & Presser, P.C.

(57) ABSTRACT

An endoscope 2 includes an insertion body 3 equipped with a potentiometer 26 for detecting a bending state of a bending portion 3B which is allowed to be bent and inserted into a subject and an electric connector 18*c* for outputting an electric signal as a detection result of the potentiometer 26, and a motor unit 4 detachable with respect to the insertion body 3 via an attachment/detachment portion 14, which is equipped with an electric motor 23 for bending the bending portion 3B.

8 Claims, 11 Drawing Sheets

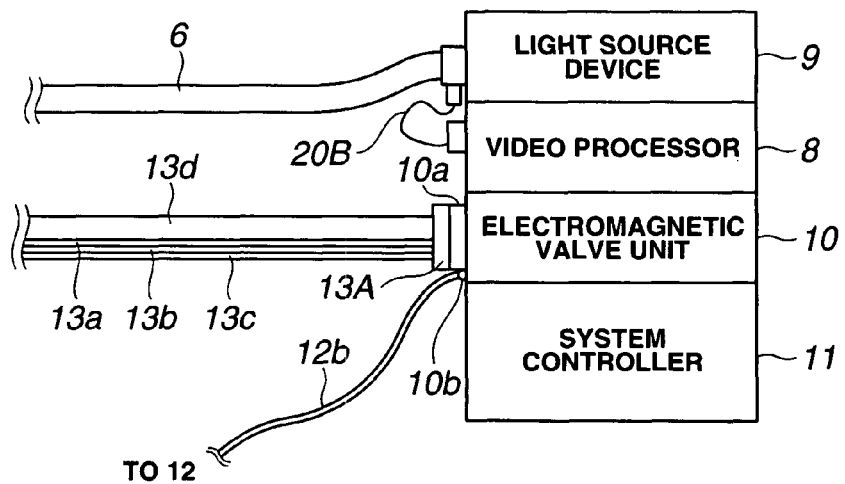
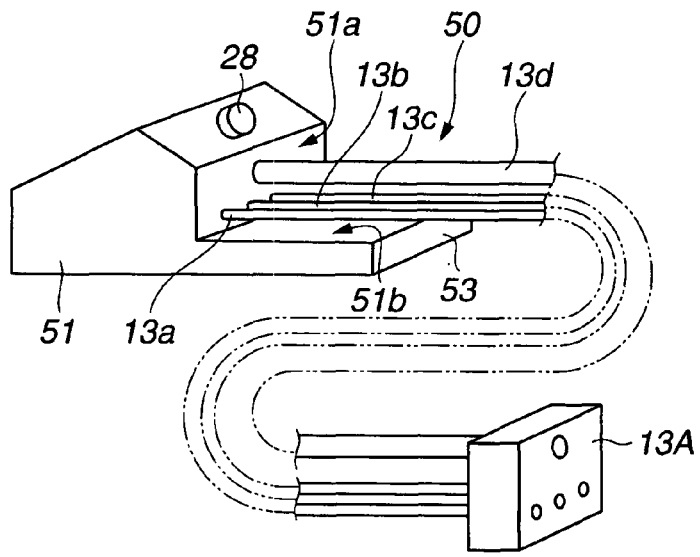
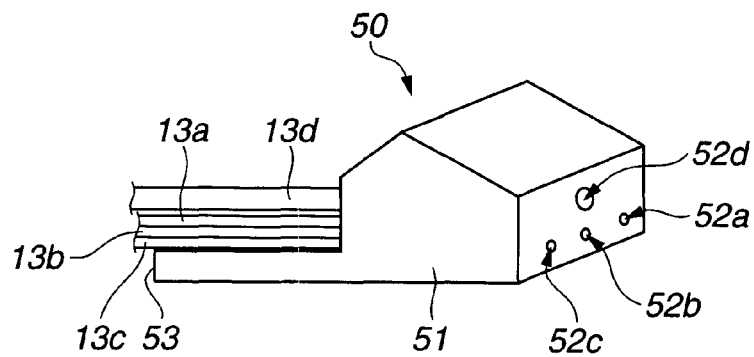

POWER DRIVEN BENDING ENDOSCOPE DEVICE WITH DETACHABLE INSERTION PORTION

CROSS REFERENCE TO RELATED APPLICATION

This application is a continuation application of PCT/JP2005/022199 filed on Dec. 2, 2005 and claims the benefit of Japanese Applications No. 2004-351803 filed in Japan on Dec. 3, 2004 and No. 2004-360320 filed in Japan on Dec. 13, 2004, the entire contents of each of which are incorporated herein by their reference.

BACKGROUND OF THE INVENTION

1. Field of the Invention

The present invention relates to a bending endoscope with detachable insertion portion provided with an insertion portion with a bending portion and a unit with bending means for bending the bending portion, which are detachably coupled.

2. Description of the Related Art

Conventionally, the endoscope has been widely used. The insertion portion of the endoscope is inserted into a body cavity such that the inside of the body cavity is observed. The treatment instrument is inserted into the channel for accommodating the treatment instrument formed in the insertion portion to perform various kinds of therapy and treatment.

Generally, the endoscope having the thin and long insertion portion includes a bending portion provided to the distal end of the insertion portion. The bending portion is structured to rotatably connect a plurality of bending pieces. The bending piece which forms the bending portion is connected to the operation wire. The bending portion is vertically or laterally bent by pulling or loosening the operation wire. The operation wire may be pulled or loosened through rotating operation of the bending knob formed on the operation portion performed by the operator, for example.

Recently, the power driven bending endoscope has been introduced, which is structured to bend the bending portion by pulling and loosening the operation wire using the bending drive means such as the electric motor. In the power driven bending endoscope, the electric motor is operated in accordance with the bending command signal outputted from the bending command means, for example, the joystick formed on the operation portion. The rotation of the electric motor is transmitted to the pulley, for example, so as to be rotated. The bending wire wound around the pulley is pulled or loosened to bend the bending portion.

Japanese Unexamined Patent Application Publication No. 6-105800 discloses the endoscope device which is structured to couple the connector with the connector bearing for guiding the power transmission output portion at the drive side provided at the enclosure of the bending motor controller and the connector at the input side formed in the connector of the endoscope to the predetermined coupled position.

In the aforementioned power driven bending endoscope, the power unit provided outside the operation portion to serve as the bending drive means is detachable with respect to the endoscope, thus reducing the size and weight of the operation portion and improving the operability.

The endoscope device disclosed in Japanese Unexamined Patent Application Publication No. 6-114001 includes a guide portion at the first joint portion disposed in the endoscope, and a guided portion at the second joint portion disposed inside the enclosure in the bending controller as the power unit. In the case where the first and the second joint portions are eccentrically connected with respect to the respective center axes, they may be coaxially connected by means of the guide portion and the guided portion.

Japanese Unexamined Patent Application Publication No. 10-234651 discloses the conduit unit attachment/detachment device as the art which relates to the conduit attachment/detachment structure. The conduit unit attachment/detachment device includes a first joint member detachably attached to the operation portion of the endoscope and a second joint member detachably attached to the electromagnetic valve unit. The first joint member is provided with a grooved rotating body and a solenoid with a fixture pin so as to be locked. The second joint member is provided with a pair of cylindrical electrodes and a pin-like electrode for the purpose of disconnecting the supply line of the drive power supply by detecting attachment/detachment state.

The lock state of the first joint member is released only when the second joint member is removed. This makes it sure to lock the conduit unit so as not to be removed during the observation with the endoscope, thus eliminating the disadvantage of interrupting the observation and treatment with the endoscope.

SUMMARY OF THE INVENTION

The bending endoscope with detachable insertion portion according to the present invention is provided with an insertion body which includes bending state detection means for detecting a bending state of a bending portion which is allowed to be bent and inserted to a subject and output means for outputting an electric signal as a detection result of the bending state detection means, and bending operation means which includes bending drive means for bending the bending portion, which is detachable with respect to the insertion body via attachment/detachment means.

BRIEF DESCRIPTION OF THE DRAWINGS

FIG. 7 is an explanatory view showing the state where the various tubes and the universal cord are connected to the external devices.

FIG. 8 is an explanatory view showing the structure of the separative conduit portion.

FIG. 9 is an explanatory view showing the structure of the connecting surface of the insertion connector which forms the separative conduit portion.

DETAILED DESCRIPTION OF THE PREFERRED EMBODIMENT(S)

Figure 1:
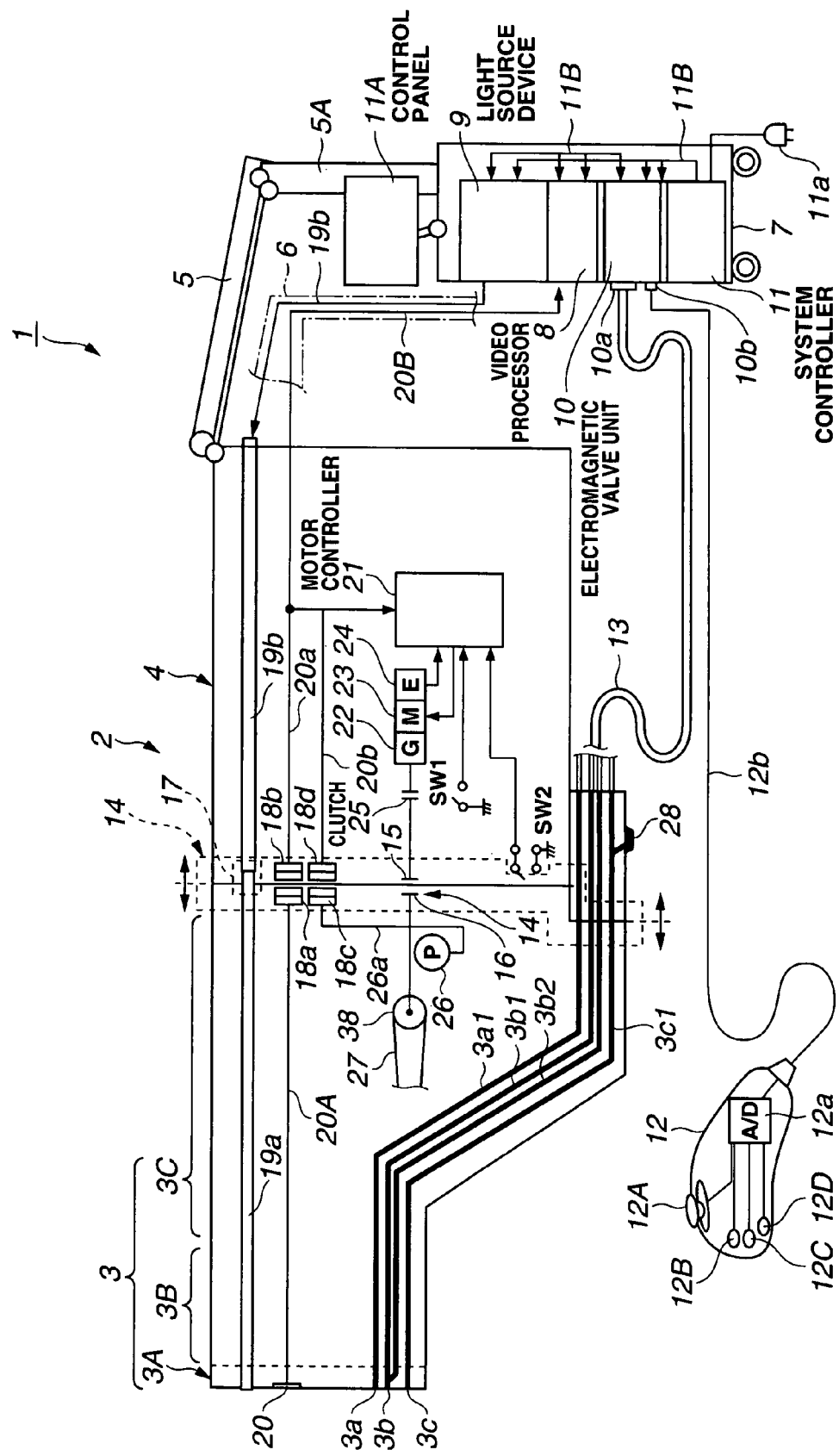
FIG. 1 is an explanatory view showing a structure of the endoscope system equipped with the power driven bending endoscope with detachable insertion portion.

Embodiments according to the present invention will be described referring to the drawings.

Embodiment 1 according to the present invention will be described referring to FIGS. 1 to 5.

Figure 2:
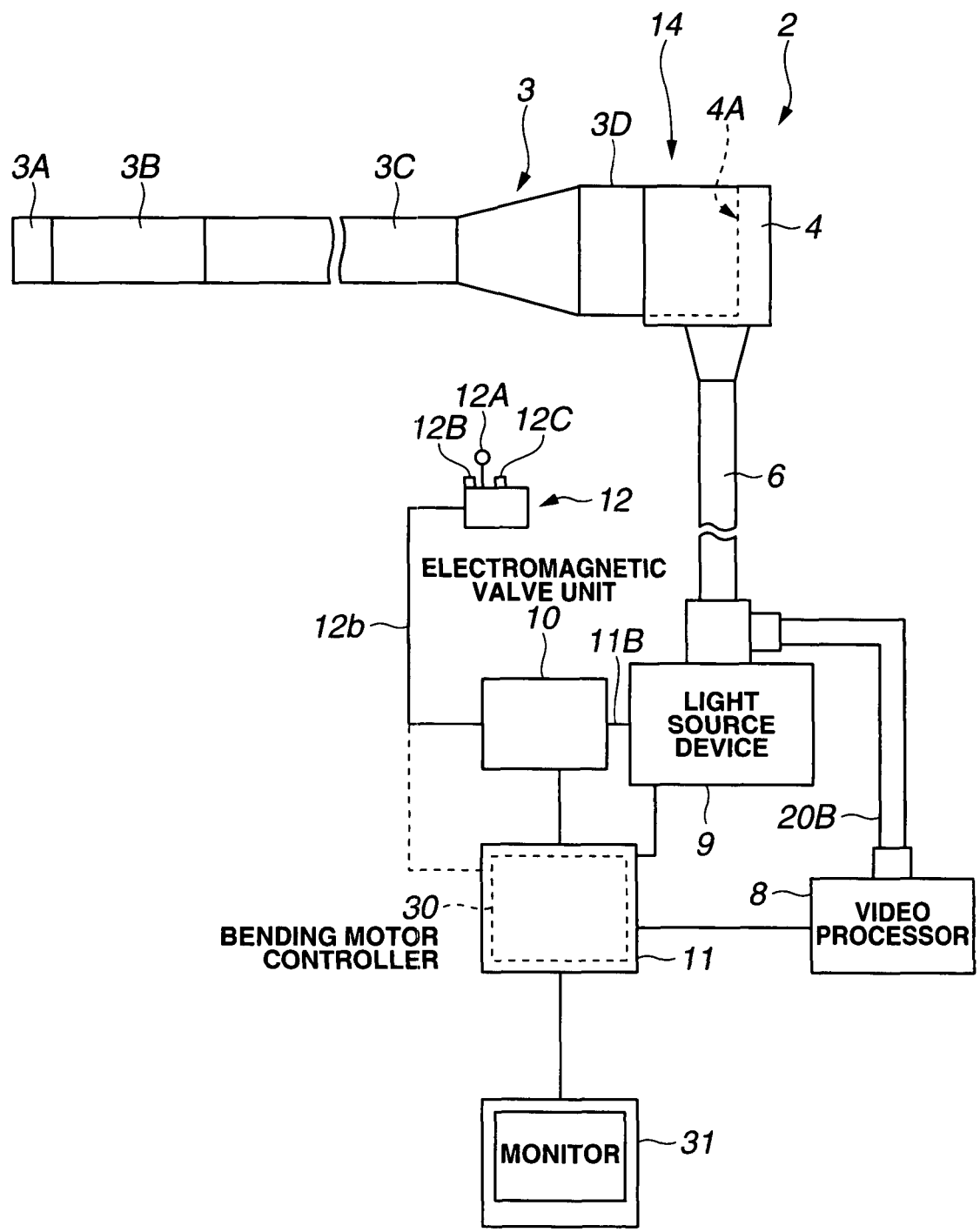
FIG. 2 is an explanatory view showing a connection between the power driven bending endoscope with detachable insertion portion and the external devices.

Referring to FIGS. 1 and 2, an endoscope system 1 is formed of a power driven bending endoscope with detachable insertion portion (hereinafter referred to as the endoscope) 2 and external devices.

The endoscope 2 is mainly formed of an insertion body 3 inserted into a subject site and a motor unit 4. The motor unit 4 is formed as the bending operation means. The motor unit 4 and the insertion body 3 are structured to be detachable as described later.

The insertion body 3 includes a distal rigid portion 3A, a bending portion 3B, a flexible tube 3C, an insertion engagement portion 3D arranged in the order from the distal end. The distal rigid portion 3A contains an image pickup device 20, for example. The bending portion 3B is bent by pulling or loosening an angle wire 27. In the case where the bending portion 3B is bent both in the vertical and lateral directions, a pair of angle wires 27 are provided. The explanation herein will be made in the case where only a single angle wire 27 is used as shown in FIG. 1.

The endoscope 2 is movably held by a scope holder 5 having a motor unit 4 detachably connected to the distal end. The proximal end of the scope holder 5 is attached to the upper portion of a cart 7. The external devices including a video processor 8, a light source device 9, an electromagnetic valve unit 10, and a system controller 11 are mounted on the cart 7.

A signal cable 20B is connected to the video processor 8 which generates the video signal from the electric signal transmitted through the signal cables 20A, 20a and 20B extending from the image pickup device 20. The video signals generated in the video processor 8 are outputted to a monitor 31 and the like as the display unit such that the image of the endoscope is displayed on the display of the monitor 31.

The light source device 9 supplies illuminating light to an illuminating optical system of the endoscope 2. Specifically, the illuminating light is transmitted through the universal cord 6, a light guide fiber 19b inserted through the motor unit 4, and a light guide fiber 19a inserted through the insertion body 3.

The electromagnetic valve unit 10 is a conduit controller, to which a signal cable 12b extending from an operation portion 12 described later and a tube 13 are connected. The electromagnetic valve unit 10 executes the fluid control, for example, air supply, water supply or suction through the tube 13, and a forward water supply conduit 3a1, air/water supply conduits 3b1 and 3b2, and a suction conduit 3c1 also serving as a forceps conduit provided in the insertion body 3.

The system controller 11 controls a motor signal controller (hereinafter referred to as a motor controller) 21 provided in the motor unit 4, and executes the entire control of the system including the video processor 8, the light source device 9, and the electromagnetic valve unit 10. The motor controller 21 serving as the control means generates a motor drive signal for driving the electric motor 23. The electric motor 23 serving as the bending drive means generates the driving force to pull and loosen the angle wire 27. The system controller 11 is electrically coupled with a control panel 11A. The operation portion provided on the display of the control panel 11A is used to give various types of operation commands to the respective devices.

The operation portion 12 serves as the operation means, and outputs such command signals as a bending command signal for bending the bending portion 3B which forms the insertion body 3, a command signal for air supply, a command signal for water supply, or a command signal for suction.

The insertion body 3 and the motor unit 4 are structured to be detachable via an attachment/detachment portion 14 as the attachment/detachment means. The attachment/detachment portion (engagement portion) 14 is provided with engagement means which enables the engagement at an arbitrary position. Specifically, the engagement means is formed of a mating clutch portion 16 at the endoscope side (hereinafter referred to as the endoscope clutch portion) as the first power transmission portion formed on the insertion body 3, and a mating clutch portion 15 at the motor unit side (hereinafter referred to as the motor clutch portion) as the second power transmission portion formed on the motor unit 4. The structure for separating into the insertion body 3 and the motor unit 4 at the attachment/detachment portion (engagement portion) 14 will be described later.

The light guide fiber 19a is provided in the insertion body 3, and the light guide fiber 19b is provided in the motor unit 4. The light guide fibers 19a and 19b are detachable by an optical connector 17 accompanied with the attachment/detachment between the insertion body 3 and the motor unit 4. When the insertion body 3 is coupled with the motor unit 4, the optical connector 17 which has been in the separated state is brought into the attachment state such that the illuminating light is transmitted. The universal cord 6 is attached to the proximal end portion of the motor unit 4. The light guide fiber 19b is inserted into the universal cord 6.

The signal cable 20A extends from the image pickup device 20. An electric connector 18a is attached to the attachment/detachment portion 14 at the insertion body 3 at the proximal end of the signal cable 20A. Meanwhile, an electric connector 18b is attached to the attachment/detachment portion 14 at the motor unit 4. The electric connector 18b is connected to the signal cable 20a. The electric connectors 18a and 18b are structured to be detachable.

When the insertion body 3 and the motor unit 4 are coupled, those two electric connectors 18a and 18b are electrically coupled, and accordingly, the signal cables 20A and the 20a are also electrically coupled.

The proximal end of the signal cable 20a is connected to the signal cable 20B disposed in the universal cord 6. Accordingly, the image pickup device 20 is electrically coupled with the video processor 8 via the signal cable 20A, the electric connectors 18a, 18b, the signal cable 20a, and the signal cable 20B.

A forward water supply opening 3a, an air/water supply opening 3b, and a suction opening 3c are formed in the distal end surface of the distal rigid portion 3A which forms the insertion body 3. Those openings are communicated with conduits 3a1, 3b1, 3b2, and 3c1 disposed in the insertion body 3. The conduits 3a1, 3b1, 3b2 and 3c1 are separated into parts corresponding to the insertion body 3 and the motor unit 4, respectively. The separated conduits 3a1, 3b1, 3b2 and 3c1 are fluid tightly communicated upon coupling of the insertion body 3 and the motor unit 4. Each end of the respective conduits at the motor unit 4 is connected to the corresponding distal end portion of the tube 13. The proximal end of the tube 13 is connected to the corresponding fluid connector. The fluid connectors are collectively provided into the fluid connector 10a of the electromagnetic valve unit 10.

A forceps insertion opening 28 communicated with the suction conduit 3c1 is formed in the motor unit 4. The treatment instrument such as the forceps is inserted into the suction conduit 3c1 through the forceps insertion opening 28 to guide the forceps through the suction opening 3c so as to perform the treatment.

The insertion body 3 includes a potentiometer 26 serving as the bending state detection means for detecting the bending state of the bending portion 3B. The potentiometer 26 detects the rotating amount of a sprocket 38 (see FIG. 5) as the pulling means formed in the insertion engagement portion 3D.

The attachment/detachment portion 14 at the insertion body 3 is provided with an electric connector 18c as the output means for outputting the rotating amount as the detection result of the potentiometer 26 to the motor unit 4. The electric connector 18c is structured to be detachably connected to an electric connector 18d as the input means formed on the attachment/detachment portion 14 at the motor unit 4.

Likewise the electric connectors 18a and 18b, those two electric connectors 18c and 18d are electrically coupled as the insertion body 3 is coupled with the motor unit 4. Accordingly, the detection signal outputted from the potentiometer 26 is inputted to the motor controller 21 in the motor unit 4 via the signal cable 26a, the electric connectors 18c, 18d and the signal cable 20b.

The signal cable 20a connected to the electric connector 18b and the motor controller 21 are electrically coupled. The signal cable 20b connected to the electric connector 18d and the motor controller 21 are electrically coupled.

In the embodiment, the electric connectors 18a and 18b for electrically coupling the image pickup device 20 with the video processor 8 are provided independently from the electric connectors 18c and 18d for electrically coupling the potentiometer 26 with the motor controller 21. However, a single electric connector may be structured to electrically coupling the image pickup device 20 with the video processor 8, and to electrically coupling the potentiometer 26 with the motor controller 21.

In the embodiment, the signal cables 20A and 20a for transmitting the image signal and the like by coupling the image pickup device 20 with the video processor 8 are provided independently from the signal cables 26a and 20b for transmitting the detection signal by coupling the potentiometer 26 with the motor controller 21. However, the signal cables 20A and 20a for coupling the image pickup device 20 with the video processor 8 may be structured to transmit the detection signal outputted from the potentiometer 26 to the motor controller 21.

When the operator operates the operation portion 12, the system controller 11 generates the bending operation signal corresponding to the operation of the operation portion 12. The bending operation signal generated in the system controller 11 is inputted to the motor controller 21 via the signal cables 20B and 20a.

The motor unit 4 includes the electric connectors 18b and 18d, the motor controller 21, the electric motor 23, an electromagnetic clutch (hereinafter referred to as the clutch) 25, a switch (SW) 1, and a switch (SW) 2 as described above. The electric motor 23 is equipped with a reduction gear 22 and an encoder 24.

The motor controller 21 controls to drive the electric motor 23. The encoder 24 serving as the driving state detection means brings the operation state of the electric motor 23, for example, the rotating speed and the rotating amount into data so as to be outputted to the motor controller 21. That is, the rotating amount or the like of the electric motor 23 is detected by the encoder 24, and the detection result is outputted to the motor controller 21.

The reduction gear 22 reduces the rotating driving force of the electric motor 23. The clutch 25 is linked with the reduction gear 22, and switches the transmission of the rotating power to the insertion body 3. The switch (SW1) detects whether the clutch 25 is in the power transmission state or the power transmission disconnection state. The switch (SW2) detects whether or not the insertion body 3 and the motor unit 4 are in the coupled state.

The bending operation signal generated in the system controller 11 is inputted to the motor controller 21 based on the command signal outputted from the operation portion 12. The motor controller 21 then generates the motor drive signal to drive the electric motor 23. Therefore, based on the detection results outputted from the encoder 24 and the detection results outputted from the potentiometer 26, the motor controller 21 generates the motor drive signal corresponding to the bending operation signal to control to drive the electric motor 23. Thus, the bending portion 3B is bent under the driving force applied from the electric motor 23.

Specifically, the driving force of the electric motor 23 is transmitted to the sprocket 38 via the motor clutch portion 15 and the endoscope clutch portion 16 of the attachment/detachment portion (engagement portion) 14. A chain 37 (see FIG. 5) connected to the angle wire 27 is wound around the sprocket 38. Accordingly, when the driving force is transmitted to the sprocket 38 to be rotated in the predetermined direction, the chain 37 is moved accompanied with the rotation of the sprocket 38. The angle wire 27 then moves forward and rearward such that the bending portion 3B is bent in accordance with the command from the operation portion 12.

The operation portion 12 includes a joystick 12A as an operation switch, and buttons 12B, 12C and 12D for controlling the fluid. The joystick 12A is used for commanding the bending operation in the vertical and lateral directions of the bending portion 3B. The button 12B is an air/water supply button to be operated for commanding the air supply and water supply. The button 12C is a suction button to be operated for commanding the suction. The button 12D is a forward water supply button to be operated for commanding the forward water supply.

The operation portion 12 contains an A/D convertor 12a therein. The A/D convertor 12a is electrically coupled with the respective operation switches 12A, 12B, 12C and 12D. The A/D converter 12a converts the operation commands from the respective operation switches 12A, 12B, 12C and 12D into the electric signals so as to be outputted to the electromagnetic valve unit 10 via the signal cable 12b and the connector 10b as the operation command signals.

The medical equipment such as the video processor 8, the light source device 9 and the electromagnetic valve unit 10 is connected to the system controller 11 via the communication cable 11B. The operation command of the joy stick 12A is inputted from the electromagnetic valve unit 10 to the system controller 11 via the communication cable 11B. Accordingly, the electromagnetic valve unit 10 is controlled based on the various operation signals of the system controller 11. The system controller 11 may be operated through the control panel 11A of touch panel type, the operation portion 12, or the remote controller (not shown). The control operation of the system controller 11 may be displayed on the control panel 11A or the monitor 31.

Referring to FIG. 2, the system controller 11 includes a bending motor controller 30. The bending motor controller 30 generates the bending operation signal based on the command signal outputted from the operation portion 12 so as to be outputted to the motor controller 21. The bending motor controller 30 outputs the bending operation signal corresponding to the operation command of the joy stick 12A of the operation portion 12 to the motor controller 21. Accordingly, the operation command signal outputted from the operation portion 12 may be transmitted to the bending motor controller 30 of the system controller 11 directly without through the electromagnetic valve unit 10. The signal cable 12b may be connected to the system controller 11 as shown by the broken line.

The separation structure of the attachment/detachment portion (engagement portion) 14 into the insertion body 3 and the motor unit 4 will be described referring to FIGS. 3 and 5.

Referring to the drawing, the endoscope 2 is provided with the attachment/detachment portion 14 for separating the endoscope 2 into the insertion body 3 and the motor unit 4. The motor clutch portion 15 is formed on the motor unit 4, and the endoscope clutch portion 16 is formed on the insertion body 3.

The motor unit 4 includes a recess-like storage portion 4A which forms the attachment/detachment portion 14. The storage portion 4A stores main portion of the insertion engagement portion 3D which forms the attachment/detachment portion 14.

The motor clutch portions 15 are formed on both side wall surfaces, which form the storage portion 4A. A plurality of protrusive engagement grooves 15a each having a tooth clutch shape as the engagement portion arranged along the rotational shaft in the radial direction so as to be engaged with the endoscope clutch portion 16 are formed on the engagement surface of the motor clutch portion 15. The electric contacts 4B and 4C as the electric connectors 18b and 18d, and the motor optical connector 17a of the optical connector 17 are formed on the back wall of the storage portion 4A.

In the state where the insertion body 3 is stored in the storage portion 4A, the electric contact 4B is brought into contact with an electric contact 3E formed on the proximal end surface of the insertion body 3 corresponding to the electric connector 18a so as to be conducted. The electric contact 4C is brought into contact with an electric contact 3F formed on the proximal end surface of the insertion body 3 corresponding to the electric connector 18c so as to be conducted. The optical connector 17a at the motor side of the optical connector 17 is connected to the optical connector 17b at the endoscope side of the optical connector 17 formed on the proximal end surface of the insertion body 3 so as to be ready for the illumination light transmission.

Engagement/disengagement buttons 34 are formed on the outer surfaces of the side walls of the motor unit 4. The engagement/disengagement state between the motor clutch portion 15 and the endoscope clutch portion 16 may be switched by operating the engagement/disengagement button 34.

Figure 5:
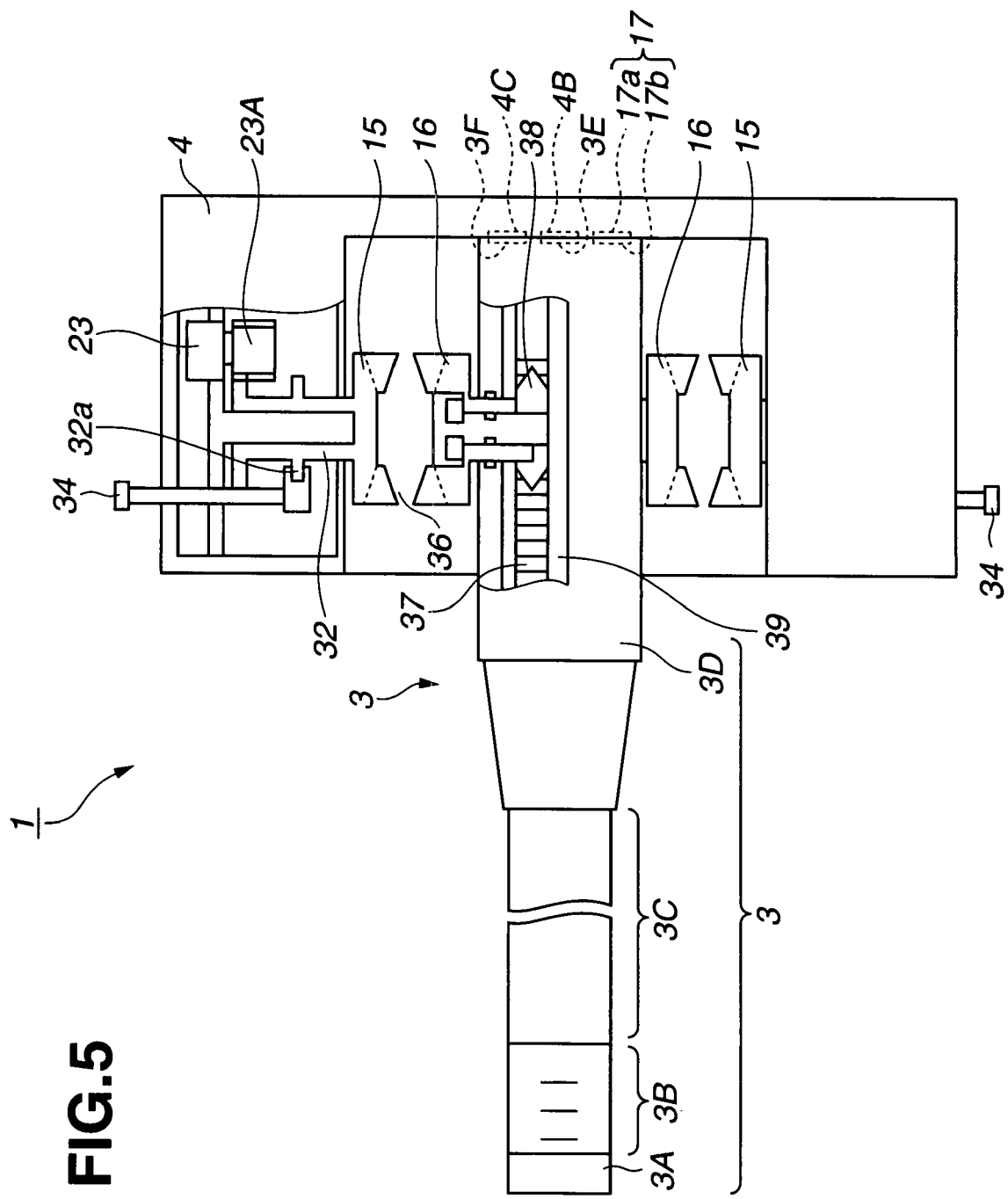
FIG. 5 is an explanatory view showing the state where the insertion body is coupled with the motor unit and the structure of the power driven bending endoscope with detachable insertion portion.

Referring to FIG. 5, the distal end portion of the engagement/disengagement button 34 is engaged with a protrusion 32a provided onto the shaft 32 of the motor clutch portion 15. The shaft 32 of the motor clutch portion 15 is movable with respect to the motor unit 4. The shaft 32 moves in the direction orthogonal to the longitudinal axial direction of the insertion body 3 which has been coupled. That is, as the engagement/disengagement button 34 is operated, the motor clutch portion 15 moves in the direction orthogonal to the longitudinal axial direction of the insertion body 3.

Meanwhile, the endoscope clutch portions 16 are provided at both sides of the insertion engagement portion 3D which form the insertion body 3. A plurality of engagement grooves 16a as engagement portions engaged with the engagement grooves 15a of the motor clutch portion 15 are formed on the engagement surface of the endoscope clutch portion 16 and arranged along the rotating shaft in the radial direction. The engagement grooves 16a and 15a are structured to have the same pitches and the same configurations.

Figure 4:
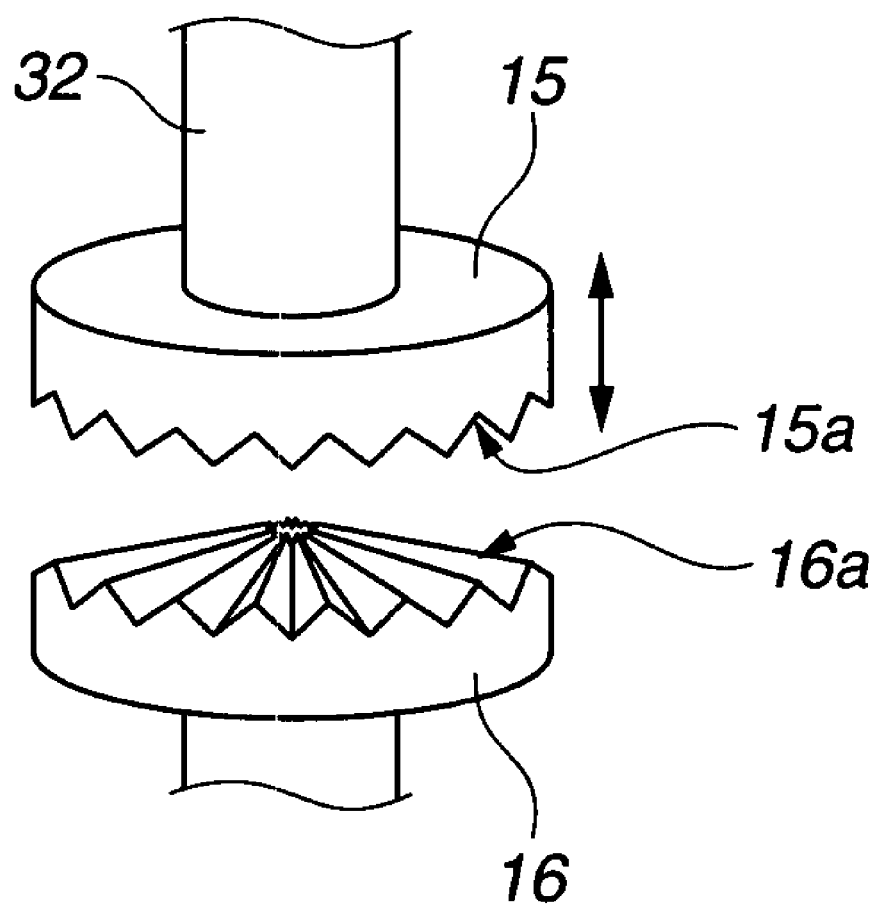
FIG. 4 is an explanatory view schematically showing the structure of the endoscope clutch portion and the motor clutch portion.

The engagement/disengagement button 34 is operated to move the motor clutch portion 15 as shown by the arrow of FIG. 4 such that the insertion body 3 is coupled with the motor unit 4. As the engagement grooves 15a of the motor clutch portion 15 have the same pitches and configurations as those of the engagement grooves 16a of the endoscope clutch portions 16, the motor clutch portion 15 and the endoscope clutch portion 16 may be brought into engagement at an arbitrary position.

The endoscope 2 of the embodiment is provided with the potentiometer 26 in the insertion body 3 of the endoscope 2. Accordingly, the rotating amount of the sprocket 38, that is, the bending angle of the bending portion 3B is always detected by the potentiometer 26. If the engagement grooves 15a of the motor clutch portion 15 and the engagement grooves 16a of the endoscope clutch portion 16 are engaged at the arbitrary position in the state where the bending portion 3B is bent, the bending control of the bending portion 3B may be reliably executed by the sprocket 38.

That is, if the insertion body 3 is coupled with the motor unit 4 in the state where the bending portion 3B is bent, the bending angle of the bending portion 3B is constantly detected by the potentiometer 26. Therefore, the operation position of the electric motor 23, the bending state of the bending portion 3B and the command position of the operation portion 12 have the intended relationship with one another. The aforementioned structure may eliminate the calibration to allow easy attachment/detachment between the insertion body 3 and the motor unit 4.

In the endoscope system 1 according to the embodiment, the motor unit 4 is equipped with the encoder 24, and the insertion body 3 is equipped with the potentiometer 26. This makes it sure to detect the bending configuration of the bending portion 3B reliably with high accuracy.

The assembly procedure of the endoscope 2 and the function of the endoscope system 1 will be described referring to FIGS. 3 to 5.

Figure 3:
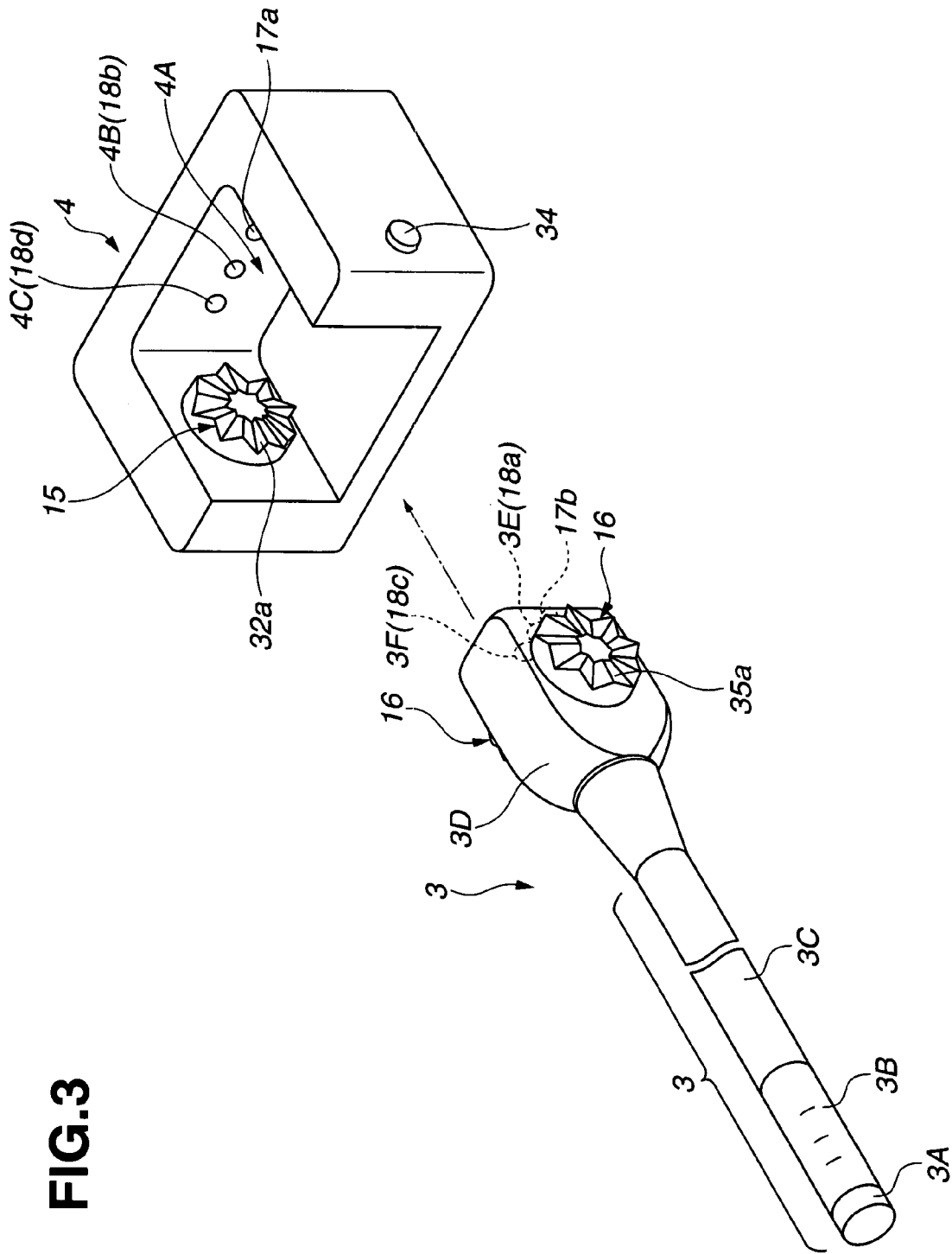
FIG. 3 is an exploded perspective view of the power driven bending endoscope with detachable insertion portion separated into the insertion body and the motor unit.

Firstly, the operator brings the separated insertion body 3 toward the direction, for example, as shown by the arrow in FIG. 3 for the purpose of assembling the endoscope 2 according to the embodiment such that the insertion body 3 is stored in the storage portion 4A of the motor unit 4. The operator brings the lower surface of the insertion engagement portion 3D as shown in the drawing into contact with the bottom surface of the storage portion 4A such that the insertion engagement portion 3D is stored in the storage portion 4A. Accordingly, the insertion engagement portion 3D of the insertion body 3 may be disposed in the storage portion 4A of the motor unit 4 as shown in FIG. 5.

The operator depresses the respective engagement/disengagement buttons 34 formed on the motor unit 4. As the engagement/disengagement button 34 is depressed, the shaft 32 of the motor clutch portion 15 moves to approach the endoscope clutch portion 16. Then the engagement grooves 15a of the motor clutch portion 15 are brought into engagement with the engagement grooves 16a of the endoscope clutch portion 16.

In the embodiment, the potentiometer 26 in the insertion body 3 is structured to constantly detect the rotating amount of the sprocket 38, that is, the bending angle of the bending portion 3B. The engagement between the motor clutch portion 15 and the endoscope clutch portion 16 at the arbitrary position is completed without performing the calibration for positioning the bending portion 3B and the joystick 12A. The insertion body 3 and the motor unit 4 are coupled to form the endoscope 2.

In the embodiment, the motor clutch portion 15 is positioned such that the axial center of the endoscope clutch portion 16 becomes coaxially opposite the axial center of the motor clutch portion 15 when the insertion engagement portion 3D is stored in the storage portion 4A. The endoscope clutch portion 16 is positioned to establish the positional relationship opposite the motor clutch portion 15 in the state where the lower surface of the insertion engagement portion 3D contacts the bottom surface of the storage portion 4A, and the proximal end surface of the insertion engagement portion 3D contacts the back wall of the storage portion 4A. The back wall of the storage portion 4A is formed as the position regulation means for bringing the motor clutch portion 15 and the endoscope clutch portion 16 into the predetermined engagement position.

When the insertion body 3 and the motor unit 4 are coupled, the electric contacts 4B and 3E become electrically conductive, and the electric contacts 4C and 3F become electrically conductive such that the motor optical connector 17a and the endoscope optical connector 17b are contacted to be ready for the illuminating light transmission. That is, the electric contacts 3E and 3F and the endoscope optical connector 17b disposed in the insertion body 3 are contacted simultaneously with the connection of the electric contacts 4B and 4C with the motor optical connector 17a.

As the electric contacts 3F and 4C are electrically coupled, the detection results of the potentiometer 26 become ready for transmission. Therefore, the detection results of the potentiometer 26 are loaded into the motor controller 21 via the signal cable 26a, the electric connectors 18c, 18d, and the signal cable 20b as shown in FIG. 1.

Meanwhile, the electric contacts 3E and 4B are electrically coupled to electrically couple the image pickup device 20 with the video processor 8 such that the drive signal and the image signal become ready for transmission. The image signal picked up by the image pickup device 20 during the observation with the endoscope is supplied to the video processor 8 via the signal cable 20A, the electric connectors 18a, 18b, and the signal cables 20a and 20B as shown in FIG. 1.

As the endoscope optical connector 17b and the motor optical connector 17a of the optical connector 17 are connected, the illuminating light supplied from the light source device 9 is irradiated to the target observation site via the light guide fiber 19b, the optical connector 17, and the light guide fiber 19a as shown in FIG. 1.

In the endoscope 2 of the embodiment where the motor clutch portion 15 is engaged with the endoscope clutch portion 16, the rotating power of the electric motor 23 shown in FIG. 5 is transmitted to the sprocket 38 connected to the endoscope clutch portion 16 via the reduction gear 22, the motor pinion 23A, the motor clutch portion 15, and the endoscope clutch portion 16.

As the sprocket 38 is rotated, the chain 37 meshed therewith is moved to pull or loosen the angle wire 27 linked with the chain 37 for bending the bending portion 3B.

The endoscope clutch portion 16 formed at the insertion engagement portion 3D and the motor clutch portion 15 formed on the motor unit 4 at the upper portion in the drawing are formed as the mechanism for bending the bending portion 3B to left and right, for example. Meanwhile, the endoscope clutch portion 16 and the motor clutch portion 15 at the lower portion in the drawing are formed as the mechanism for bending the bending portion 3B up and down.

The procedure for separating the endoscope 2 into the insertion body 3 and the motor unit 4 will be described.

The operator stops the electric motor 23 for the purpose of separating the endoscope 2 into the insertion body 3 and the motor unit 4. In the aforementioned state, the respective engagement/disengagement buttons 34 are returned. As the distal end portion of the engagement/disengagement button 34 moves, the shaft 32 of the motor clutch portion 15 moves in the direction away from the endoscope clutch portion 16. As a result, the motor clutch portion 15 is disengaged from the endoscope clutch portion 16. The operator then grasps the insertion body 3 to be brought to the direction reverse of the arrow in the drawing such that the insertion body 3 is detached from the storage portion 4A of the motor unit 4.

The endoscope 2 of the embodiment is provided with the potentiometer 26 in the insertion body 3. The potentiometer 26 detects the rotating amount of the sprocket 38 to constantly detect the bending angle of the bending portion 3B. Even if the bending portion 3B is already bent, the bending state of the bending portion 3B may be obtained by the potentiometer 26 in the state where the motor clutch portion 15 is engaged with the endoscope clutch portion 16 to make it sure to execute the position control of the sprocket 38. In the case where the insertion body 3 and the motor unit 4 are coupled with no consideration with the state of the bending portion 3B upon the coupling operation, the calibration operation is not required. The attachment/detachment between the insertion body 3 and the motor unit 4 may be easily performed.

The motor unit 4 is equipped with the encoder 24 for detecting the rotating amount of the electric motor 23. The insertion body 3 is equipped with the potentiometer 26 for detecting the rotating amount of the sprocket 38. This makes it sure to control the bending state of the bending portion 3B in accordance with the operation command through the joystick 12A based on the rotating amount of the electric motor 23 and the rotating amount of the sprocket 38 with high accuracy.

In the embodiment, the potentiometer 26 for detecting the rotating amount of the sprocket 38 is used as the detection means for detecting the bending state of the bending portion 3B. However, the detection means for detecting the bending state of the bending portion 3B is not limited to the potentiometer 26. For example, the bending state detection means for detecting the position of the angle wire 27 by detecting the magnetic field using the coil and magnetic substance may be used. Alternatively, the bending state detection means formed of the optical sensor and the marking at a predetermined position on the angle wire 27 may be used.

In the embodiment, the engagement/disengagement buttons 34 are provided for the vertical and lateral movements so as to be independently operated. However, one of the engagement/disengagement buttons or a single operation button may be structured to move the motor clutch portion 15. The engagement state and the disengagement state between the motor clutch portion 15 and the endoscope clutch portion 16 corresponding to the vertical and the lateral movements may be switched by operating only the single engagement/disengagement button.

In the embodiment, the switching operation between the engagement and disengagement states with the engagement/disengagement buttons 34 may be mechanically performed. However, the switching operation with the engagement/disengagement buttons 34 may be electrically performed.

In the embodiment, the endoscope clutch portion 16 and the motor clutch portion 15 have engagement grooves 15a and 16a of tooth clutch type, respectively. However, the clutch portions 15 and 16 are not limited to those having the engagement grooves 15a and 16a. They may be formed into arbitrary configurations to allow the power transmission.

In the embodiment, two conduits, that is, the forward water supply conduit 3a1 and the water supply conduit 3b2 are provided. However, the number of the water supply conduits is not limited to two, but may be set to one or the number equal to or larger than two. In this case, the water supply conduit communication portion and the water supply tube may be provided corresponding to the number of the water supply conduits.

Embodiment 2 according to the present invention will be described referring to FIGS. 6 to 14.

Figure 6:
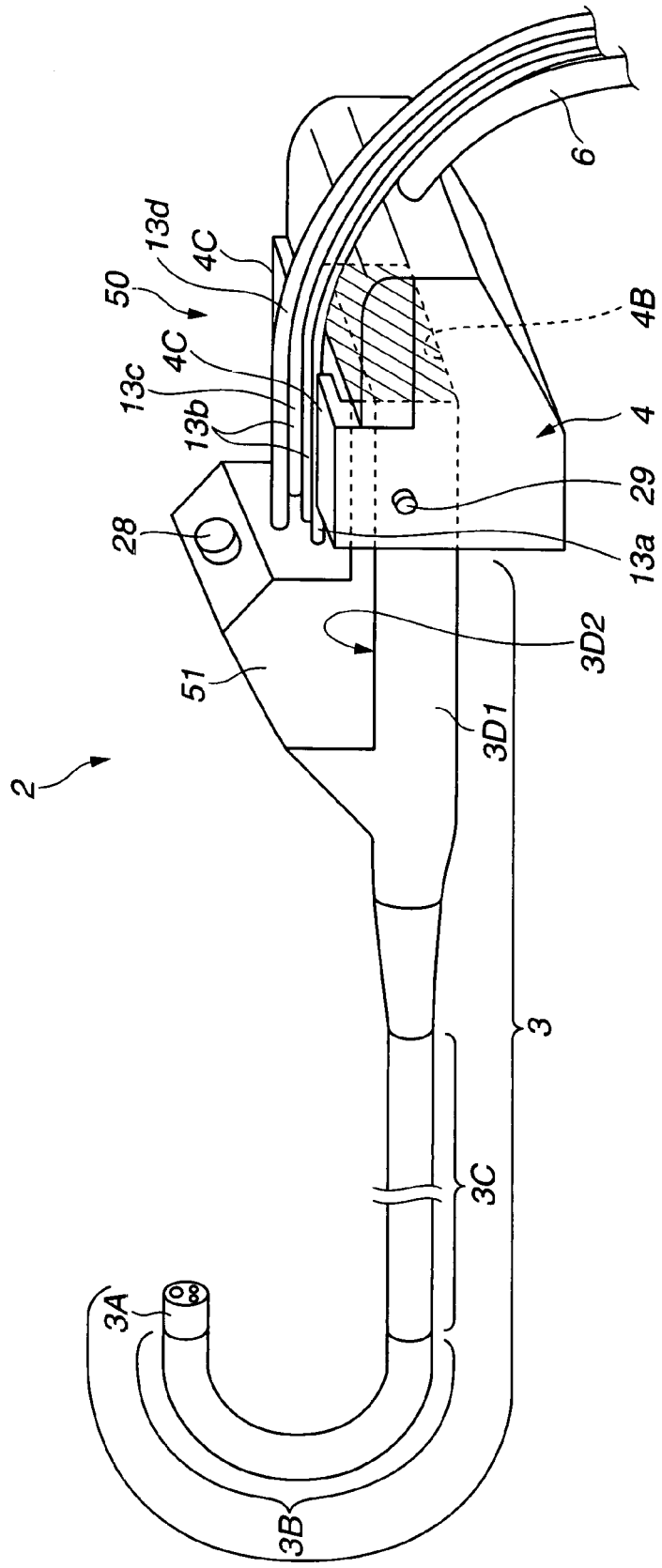
FIG. 6 is an explanatory view showing the structure of the power driven bending endoscope with detachable insertion portion including the separative conduit portion.

Referring to FIG. 6, in the endoscope 2 of the embodiment, a separative conduit 50 having a tube insertion connector 51 is detachable with respect to the insertion engagement portion 3D1 which forms the insertion body 3.

The predetermined fluid is supplied to the forward water supply conduit 3a1, the air/water supply conduits 3b1, 3b2 and the suction conduit 3c1 in the insertion body 3 via the corresponding tubes 13a, 13b, 13c and 13d. The proximal ends of the tubes 13a, 13b, 13c and 13d are collectively detachable with respect to the fluid connector portion 10a of the electromagnetic valve unit 10 via a tube connector 13A as shown in FIG. 7, for example.

The separative conduit 50 is detachably fit with an insertion connector 3D2 formed in the notch of the insertion engagement portion 3D1 at the proximal end of the insertion body 3 of the endoscope 2.

Referring to FIGS. 6, 8 and 9, the separative conduit 50 is formed of the tube insertion connector 51 and the tubes 13a, 13b, 13c and 13d each distal end of which is fixed to the tube insertion connector 51 so as to be communicated therewith. Referring to FIG. 6, the tubes 13a, 13b, 13c and 13d are communicated with the respective conduits 3a1, 3b1, 3b2 and 3c1 inserted through the insertion body 3 in the state where the tube insertion connector 51 that forms the separative conduit 50 is fit with the insertion connector 3D2 of the insertion engagement portion 3D1.

The insertion engagement portion 3D1 is detachable with respect to the motor unit 4 in the state where the tube insertion connector 51 is fit with the insertion connector 3D2 of the insertion engagement portion 3D1, which will be described later in detail.

Figure 10:
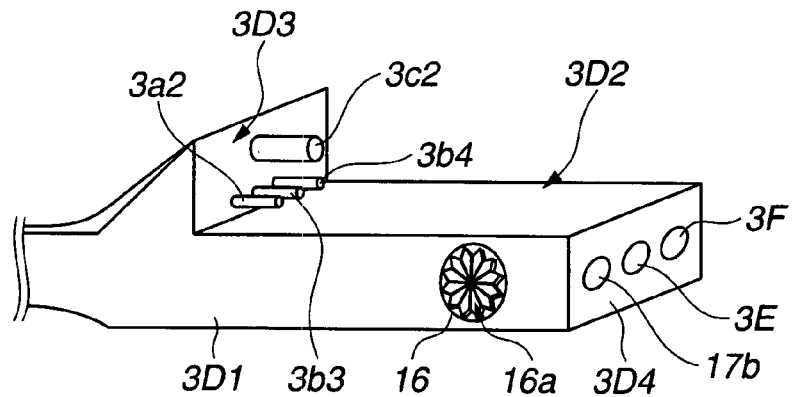
FIG. 10 is a perspective view showing the structure of an insertion engagement portion in the state where the separative conduit portion is disconnected.

Referring to FIG. 10, the endoscope clutch portions 16 are formed on both sides of the insertion engagement portion 3D1 of the embodiment. A forward water supply conduit communication portion 3a2, an air supply conduit communication portion 3b3, a water supply conduit communication portion 3b4, and a suction conduit communication portion 3c2 are formed on a standing surface 3D3 which constitutes the insertion connector 3D2 of the insertion engagement portion 3D1. The forward water conduit communication portion 3a2 is communicated with the forward water supply conduit 3a1, the air supply conduit communication portion 3b3 is communicated with the air/water supply conduit 3b1, the water supply conduit communication portion 3b4 is communicated with the air/water supply conduit 3b2, and the suction conduit communication portion 3c2 is communicated with the suction conduit 3c1.

Referring to FIG. 9, the forward water supply port 52a, the air supply port 52b, the water supply port 52c and the suction port 52d are formed in the top end surface as the connecting surface of the tube insertion connector 51. The forward water supply port 52a is fit with the forward water supply conduit communication portion 3a2, the air supply port 52b is fit with the air supply conduit communication portion 3b3, the water supply port 52c is fit with the water supply conduit communication portion 3b4, and the suction port 52d is fit with the suction conduit communication portion 3c2, respectively.

Referring to FIGS. 9 and 10, the forward water supply port 52a serves as a distal end opening of the through hole which forms the forward water supply conduit 3a1. The proximal end opening of the through hole is communicated with the forward water supply tube 13a. The air supply port 52b serves as a distal end opening of the through hole which forms the air supply conduit 3b1. The air supply tube 13b is communicated with the proximal end opening of the through hole. The water supply port 52c serves as a distal end opening of the through hole which forms the water supply conduit 3b2. The water supply tube 13c is communicated with the proximal end opening of the through hole. The suction port 52d serves as a distal end opening of the through hole which forms the suction conduit 3c1. The suction tube 13d is communicated with the proximal end opening of the through hole. The reference numeral 53 represents the abutment surface.

Each proximal end opening is formed on the standing surface 51a of the notch formed in the tube insertion connector 51. Accordingly, the tubes 13a, 13b, 13c and 13d respectively connected to the proximal end portions are formed on the notch. Referring to FIG. 6, the conduits 3a1, 3b1, 3b2 and 3c1 are communicated with the corresponding tubes 13a, 13b, 13c and 13d when the tube insertion connector 51 is coupled with the insertion body 3.

Figure 11:
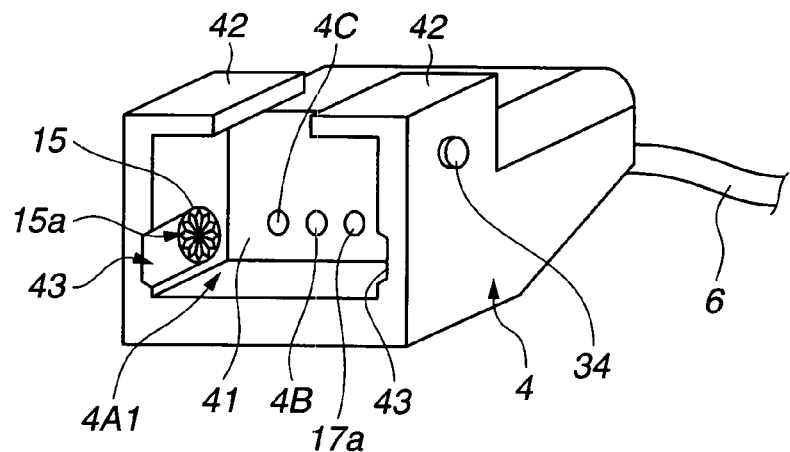
FIG. 11 is an explanatory view showing the connecting portion formed on the back wall of the motor unit.

The electric contacts 3E, 3F and the endoscope optical connector 17b are formed on the proximal end surface 3D4 of the insertion connector 3D1. When the insertion connector 3D1 is coupled with the motor unit 4, the electric contacts 3E, 3F and the endoscope optical connector 17b are coupled with the electric contacts 4B, 4C and the motor optical connector 17a as shown in FIG. 11. The electric connectors 4B, 4C and the motor optical connector 17a are formed at the predetermined positions on the back wall 41 serving as the position regulating means of the storage portion 4A1 of the motor unit 4.

Referring to FIG. 8, the proximal ends of the tubes 13a, 13b, 13b and 13c each extending from the proximal end surface of the tube insertion connector 51 are formed as the tube connector 13A as shown in FIG. 8. The plural tubes 13a, 13b, 13b and 13c may be attached/detached in one operation by attaching/detaching the tube connector 13A to/from the fluid connector portion 10a of the electromagnetic valve unit 10.

The reference numeral 28 shown in FIGS. 6 and 8 denotes the forceps insertion opening. The forceps insertion opening 28 is formed on the upper surface of the tube insertion connector 51 so as to be communicated with the through hole which constitutes the suction conduit 3*c*1.

Figure 12:
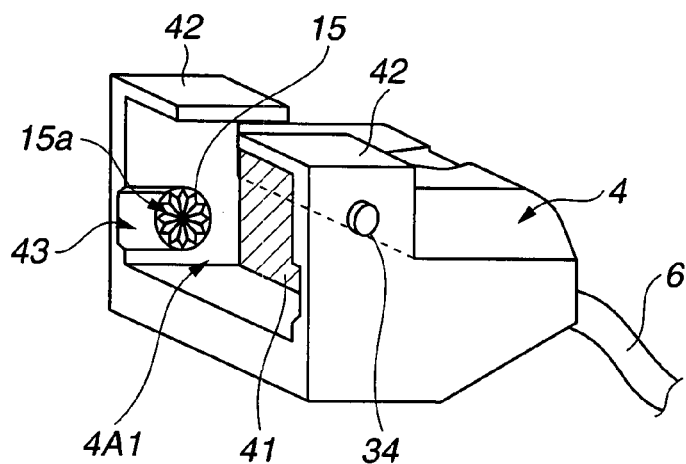
FIG. 12 is an explanatory view showing the structure of the storage portion including the back wall of the motor unit.
Figure 13:
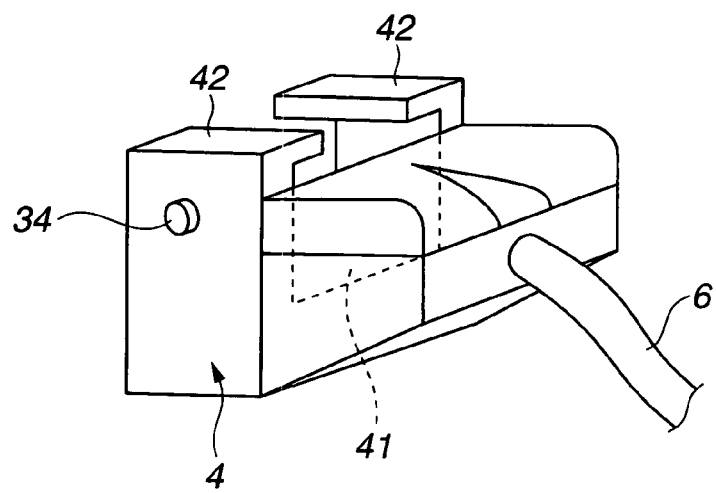
FIG. 13 is a perspective view showing the structure of the back surface of the motor unit.

Referring to FIGS. 11, 12 and 13, the motor unit 4 includes the storage portion 4A1 which stores the integrally combined insertion engagement portion 3D1 and the tube insertion connector 51. A back wall 41 is formed as the position regulating means to the back of the storage portion 4A1. The tube insertion connector 51 and the insertion engagement portion 3D1 abut against the back wall 41 so as to regulate the arrangement position.

An engagement guide portions 42 are formed above the storage portion 4A1 as shown in the drawing. The engagement guide portions 42 are bent at the storage portion 4A1. The engagement guide portions 42 guide a plane 51*b* of the notch formed in the tube insertion connector 51 to prevent the tube insertion connector 51 from being removed upward of the motor unit 4.

The motor clutch portions 15 are formed on both side walls which form the storage portion 4A1. Guide grooves 43 are formed in both side walls of the storage portion 4A1 to the front of the motor clutch portions 15.

The guide grooves 43 are used for guiding the integrally combined insertion engagement portion 3D1 and the tube insertion connector 51 to the predetermined position in the storage portion 4A1. The guide groove 43 for guiding the insertion engagement portion 3D1 and the like, and the back wall 41 against which the insertion engagement portion 3D1 abuts are provided to make it sure to engage the endoscope clutch portion 16 at the engagement position.

The engagement/disengagement buttons 34 for switching the engagement/disengagement state between the motor clutch portion 15 and the endoscope clutch portion 16 are provided on both side surfaces of the motor unit 4. The universal cord 6 extends from the proximal end surface of the motor unit 4, for example.

The procedure for assembling the endoscope 2 will be described referring to FIGS. 7 to 12.

Firstly, the operator disposes the tube insertion connector 51 of the separative conduit 50 separated as shown in FIG. 8 on the insertion connector 3D2 which forms the insertion engagement portion 3D1 shown in FIG. 10. Thereafter, the tube insertion connector 51 is coupled with the insertion engagement portion 3D1 through the sliding movement.

In this case, the operator brings the forward water supply port 52*a*, the air supply port 52*b*, the water supply port 52*c* and the suction port 52*d* formed on the connecting surface of the tube insertion connector 51 shown in FIG. 9 into communication with the forward water supply conduit communication portion 3*a*2, the air supply conduit communication portion 3*b*3, the water supply conduit communication portion 3*b*4, and the suction/forceps conduit communication portion 3*c*2 formed on the standing surface 3D3 of the insertion engagement portion 3D1.

The forward water supply conduit 3*a*1, the air supply conduit 3*b*1, the water supply conduit 3*b*2 and the suction conduit 3*c*1 are communicated with the forward water supply tube 13*a*, the air supply tube 13*b*, the water supply tube 13*c*, and the suction tube 13*d* through a plurality of through holes (not shown) formed in the tube insertion connector 51.

Next, the operator attaches the integrally combined tube insertion connector 51 and the insertion engagement portion 3D1 to the motor unit 4. The operator slides the predetermined portion of the insertion engagement portion 3D1, which is overlapped with the tube insertion connector 51 so as to be inserted into the storage portion 4A1 while being disposed in the guide groove 43 of the motor unit 4. The tube insertion connector 51 is guided by the engagement guide portions 42 of the motor unit 4. The operator slides the integrally combined tube insertion connector 51 and the insertion engagement portion 3D1 into the storage portion 4A1 until the proximal end surface 3D4 of the insertion engagement portion 3D1 and the abutment surface 53 of the tube insertion connector 51 abut against the back wall 41 of the motor unit 4.

The proximal end surface 3D4 of the insertion engagement portion 3D1 and the abutment surface 53 of the tube insertion connector 51 abut against the back wall 41 of the motor unit 4. At this time, the endoscope clutch portion 16 of the insertion engagement portion 3D1 and the motor clutch portion 15 of the motor unit 4 are positioned to make it sure to be engaged.

Thereafter, the operator operates the engagement/disengagement button 34 to move the motor clutch portion 15 toward the endoscope clutch portion 16. The engagement groove 15*a* of the motor clutch portion 15 is engaged with the engagement groove 16*a* of the endoscope clutch portion 16 to be ready for the power transmission. The assembly of the endoscope 2 of the embodiment, thus, is completed.

Next, the procedure for separating the endoscope 2 shown in FIG. 6 into the insertion body 3, the separative conduit 50, and the motor unit 4 will be described.

The operator returns the engagement/disengagement buttons 34 formed on the motor unit 4 after confirming that the electric motor 23 is stopped. As the engagement/disengagement button 34 is returned, the motor clutch portion 15 is moved in the direction away from the endoscope clutch portion 16. The motor clutch portion 15 and the endoscope clutch portion 16, thus, are disengaged.

Then the operator grasps the insertion engagement portion 3D1 and the tube insertion connector 51 to be moved leftward in the drawing. Accordingly, the integrally combined insertion engagement portion 3D1 and the tube insertion connector 51 are separated from the motor unit 4.

The tube insertion connector 51 which forms the separative conduit 50 is detached from the insertion engagement portion 3D1 in the reverse order of the assembly as described above. The separation of the endoscope 2, thus, is completed.

In the embodiment, the tube insertion connector 51 which forms the seaprative conduit 50 and the insertion engagement portion 3D1 integrally combined therewith are stored in the storage portion 4A1 of the motor unit 4. The storage operation is performed by regulating the tube insertion connector 51 in the direction so as not to be fallen off with the back wall 41. This makes it sure to prevent the tube insertion connector 51 which forms the separative conduit 50 from falling off the insertion body 3. Therefore, the operator is allowed to perform the observation and treatment with the endoscope 2 without caring about falling off of the tube and the like. Unlike the related art, the separative conduit 50 is structured to prevent the insertion engagement portion 3D1 from falling off the motor unit 4 without fixing pin nor solenoid, thus preventing enlargement and complexity of the separative conduit 50 and the cost increase.

The back wall 41 formed on the storage portion 4A1 easily allows the endoscope clutch portion 16 of the insertion engagement portion 3D1 and the motor clutch portion 15 of the motor unit 4 to be in the engagement position. This makes it sure to perform the power transmission from the motor unit 4 to the insertion body 3.

Figure 14:
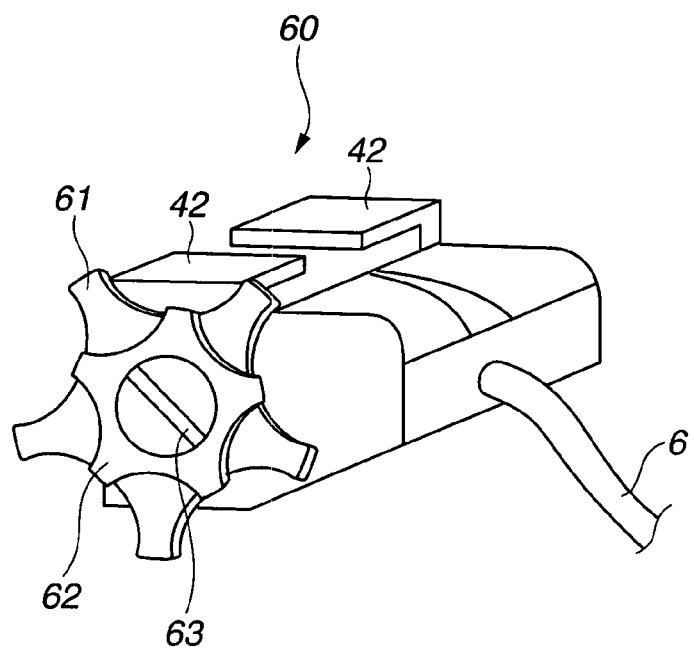
FIG. 14 is an explanatory view showing the structure of the bending operation unit for bending the bending portion of the power driven bending endoscope with detachable insertion portion.

In the embodiment, the command for bending the bending portion 3B through the operation portion 12, and the power driven bending endoscope which electrically bends the bending portion 3B based on the command have been described. However, the structure of the endoscope is not limited to the one as described above. For example, a bending operation unit 60 including a bending knob 61 for the vertical direction, a bending knob 62 for the lateral direction and an engagement knob 63 as shown in FIG. 14 may be structured as the endoscope for manually operating the bending portion 3B. The bending operation unit 60 as the bending operation means is equipped with a bending operation mechanism unit as the bending drive means (not shown) in the insertion body for operating the bending drive mechanism such as the sprocket around which the bending operation wire is wound. The bending operation mechanism unit is connected to the bending knobs 61, 62 and the engagement knob 63 in the bending operation unit 60.

Embodiment 3 according to the present invention will be described referring to FIGS. 15 to 17.

In the endoscope 2 of the embodiment, the direction in which an integrally combined insertion engagement portion 3D5 and tube insertion connector 56 are attached to the motor unit 4 is different from that of Embodiment 2. Specifically, in Embodiment 2, the integrally combined insertion engagement portion 3D1 and the tube insertion connector 51 are horizontally moved so as to be attached to the motor unit 4. In the embodiment, they are vertically moved to be attached to the motor unit 4.

Figure 15:
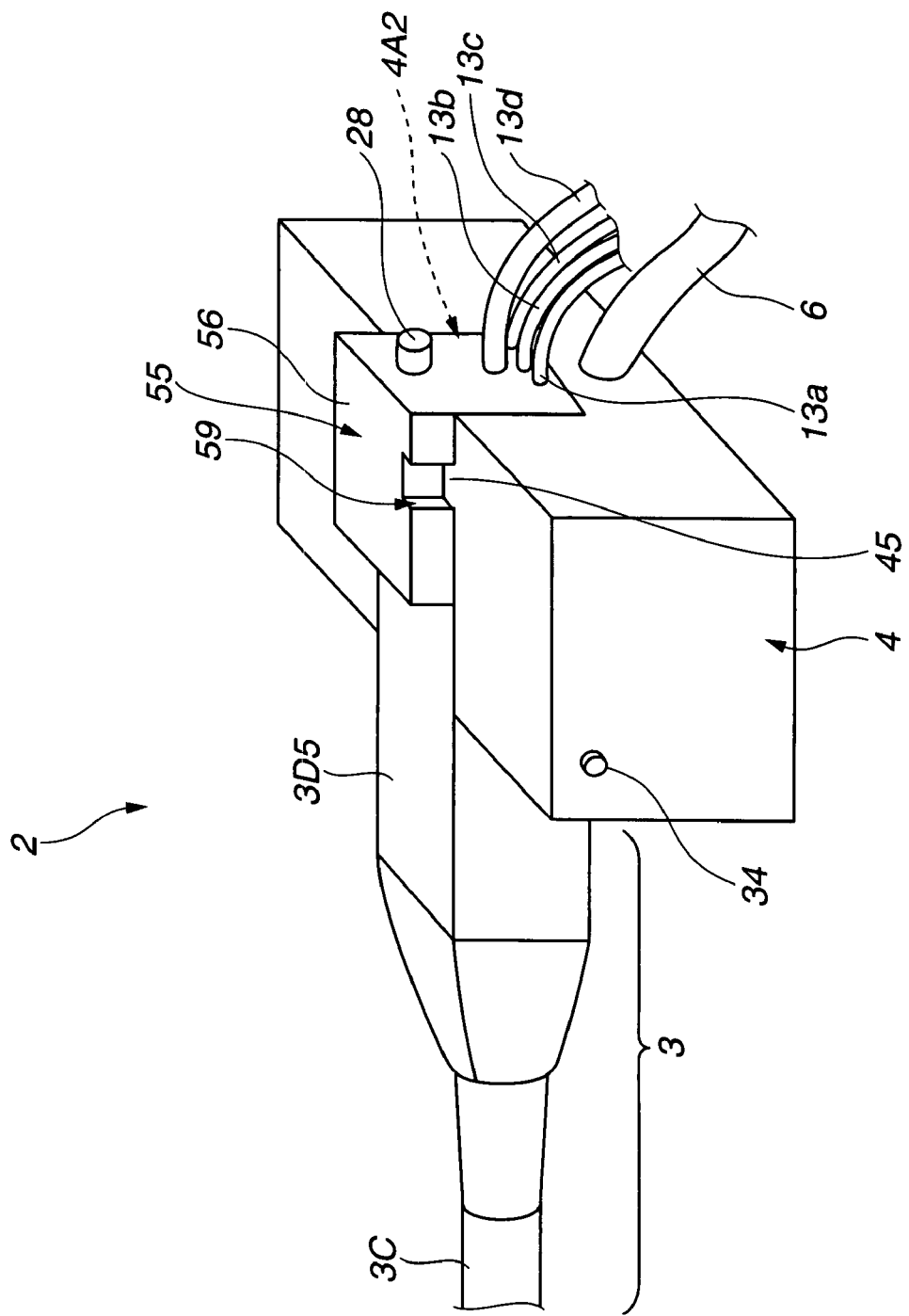
FIG. 15 is an explanatory view showing another structure of the power driven bending endoscope with detachable insertion portion which includes the separative conduit portion.

Referring to FIG. 15, the endoscope 2 of the embodiment is formed of the insertion body 3 including the insertion engagement portion 3D5, a separative conduit 55 including the tube insertion connector 56, and the motor unit 4.

Figure 16:
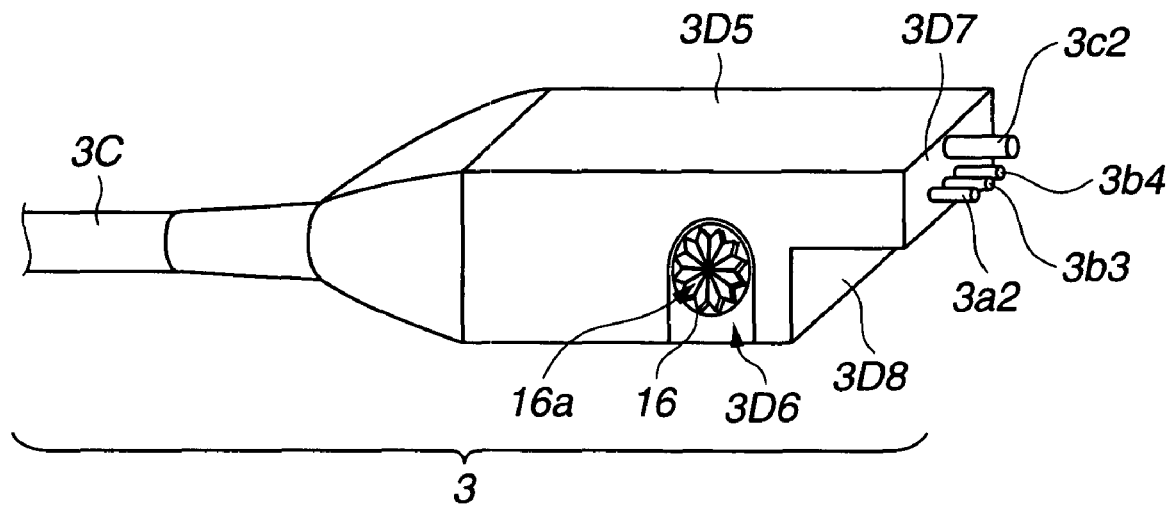
FIG. 16 is a perspective view showing the structure of the insertion engagement portion in the state where the separative conduit portion is disconnected.

Referring to FIG. 16, a notch is formed at the lower portion of the proximal end of the insertion engagement portion 3D5. The endoscope clutch portions 16 and the guide grooves 3D6 are formed on both side surfaces of the insertion engagement portion 3D5. Openings of the guide grooves 3D6 coincide with respect to the insertion direction, that is, the lower portion in the drawing. Referring to FIG. 17, guide grooves 59 with which protrusions 45 formed on both side surfaces of the storage portion 4A1 of the motor unit 4 are fit are formed.

A forward water supply conduit communication portion 3a2, an air supply conduit communication portion 3b3, a water supply conduit communication portion 3b4, and a suction/forceps conduit communication portion 3c2 are formed in a proximal end surface 3D7 of the insertion engagement portion 3D5.

Figure 17:
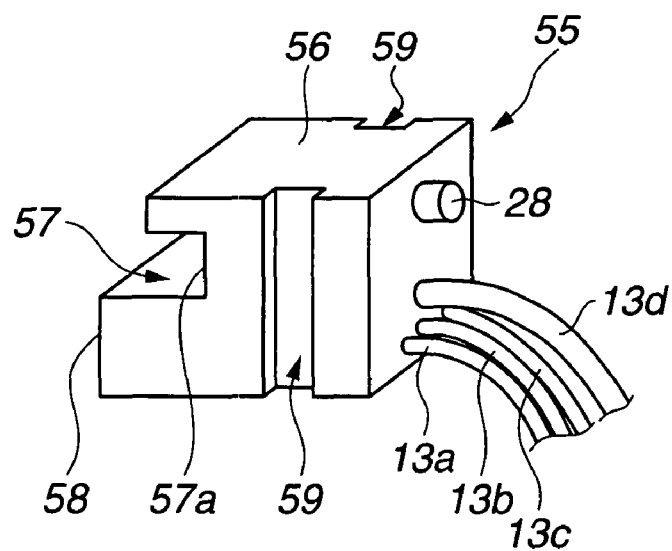
FIG. 17 is an explanatory view showing the structure of the insertion connector which forms the separative conduit.

Those conduit communication portions 3a2, 3b3, 3b4 and 3c2 are communicated with ports 52a, 52b, 52c and 52d (not shown) formed on the connecting surface 57a of the tube insertion connector 56 shown in FIG. 17.

The notch of the insertion engagement portion 3D5 includes an abutment surface 3D8. In the state where the insertion engagement portion 3D5 is integrally combined with the tube insertion connector 56, the abutment surface 3D8 abuts the abutment surface 58 of the tube insertion connector 56.

Likewise Embodiment 2, the tubes 13a, 13b, 13c and 13d are provided to the tube insertion connector 56 which is combined to the insertion engagement portion 3D5. The respective tubes 13a, 13b, 13c and 13d extending from the tube insertion connector 56 are communicated with through holes (not shown) formed in the tube insertion connector 56. The forceps insertion opening 28 is formed around the top end portions of the tubes 13a, 13b, 13c and 13d, for example, at the top surface portion.

A groove 57 with which the proximal protrusion of the insertion engagement portion 3D5 is fitted is formed in the tube insertion connector 56. The guide grooves 59 fit with the protrusions 45 formed on both side surfaces of the storage portion 4A2 of the motor unit 4 to be described later are formed on both side surfaces of the tube insertion connector 56.

In the embodiment, the connecting surface 57a of the groove 57, the abutment surface 58 and the guide groove 59 formed in the seaprative conduit 55, and the bottom surface of the storage portion 4A1 of the motor unit 4 serve as the position regulating means. It is possible to regulate the tube insertion connector 56 in the direction so as not to be fallen off with respect to the motor unit 4. This makes it sure to prevent the tube insertion connector 56 from falling off in the horizontal direction of the motor unit 4.

Meanwhile, the motor unit 4 includes the storage portion 4A2 as shown in FIG. 15. The integrally combined insertion engagement portion 3D5 and the tube insertion connector 56 are detachable with respect to the storage portion 4A2. The opening of the storage portion 4A2 is formed upward of the motor unit 4 in the drawing. That is, the integrally combined insertion engagement portion 3D5 and the tube insertion connector 56 are fit with the storage portion 4A2 from above referring to the drawing.

The protrusions 45 fit with the guide grooves 59 formed in the tube insertion connector 56 are formed on both side surfaces of the storage portion 4A1. Protrusion (not shown) engaged with the guide groove 3D6 of the insertion engagement portion 3D5 and a motor clutch portion (not shown) disposed above the protrusion are formed at the portion closer to the distal end portion of the insertion body 3 than the protrusions 45.

In the embodiment, lock means may be disposed on the upper surface of the motor unit 4 to hold the insertion engagement portion 3D5 and the tube insertion connector 56 which are stored in the storage portion 4A2 so as not to be fallen off from above. Other structures are the same as those of Embodiment 2.

Next, the procedure for assembling the endoscope 2 according to the embodiment will be described referring to FIGS. 15 to 17.

Firstly, the operator fits the proximal end protrusion of the insertion engagement portion 3D5 shown in FIG. 16 with a groove 57 formed in the tube insertion connector 56 which forms the separative conduit portion 55 which has been separated as shown in FIG. 17. The operator then communicates the ports 52a, 52b, 52c and 52d with the forward water supply conduit communication portion 3a2, the air supply conduit communication portion 3b3, the water supply conduit communication portion 3b4, and the suction/forceps conduit communication portion 3c2.

The forward water supply conduit 3a1, the air supply conduits 3b1, 3b2, and the suction conduit 3c1 are communicated with the forward water supply tube 13a, the air supply tube 13b, the water supply tube 13c, and the suction tube 13d through a plurality of through holes (not shown) formed in the tube insertion connector 56.

The operator then attaches the integrally combined tube insertion connector 56 and the insertion engagement portion 3D5 to the motor unit 4. In the state where the tube insertion connector 56 is fitted in the horizontal direction of the insertion engagement portion 3D5, the storage is performed in the storage portion 4A2 from above the motor unit 4. Then the guide grooves 59 of the tube insertion connector 56 are engaged with the protrusions 45 of the motor unit 4. Thus, the integrally combined tube insertion connector 56 and the insertion engagement portion 3D5 are slidably guided to be stored into the storage portion 4A2.

The operator slides the integrally combined tube insertion connector 56 and the insertion engagement portion 3D5 into the storage portion 4A1 until the lower surfaces of the insertion engagement portion 3D5 and the tube insertion connector 56 abut against the bottom surface of the storage portion 4A2 of the motor unit 4.

In the embodiment, the integrally combined tube insertion connector 56 and the insertion engagement portion 3D5 are positioned by the connecting surface 57a of the groove 57 formed in the tube insertion connector 56, the abutment surface 58 and the guide groove 59 formed in the tube insertion connector 56, and the bottom surface of the storage portion 4A1 of the motor unit 4. The lower surfaces of the insertion engagement portion 3D5 and the tube insertion connector 56 abut against the bottom surface of the storage portion 4A1. This makes it sure to dispose the endoscope clutch portion 16 formed on the insertion engagement portion 3D5 and the motor clutch portion 15 formed on the motor unit 4 at the engagement position.

The operator then operates to depress the engagement/disengagement button 34 shown in FIG. 15. Then the engagement groove 15a of the motor clutch portion 15 and the engagement groove 16a of the endoscope clutch portion 16 are engaged to be ready for the power transmission. The assembly of the endoscope 2, thus, is completed.

Next, when the endoscope 2 shown in FIG. 15 is separated into the insertion body 3, the separative conduit 55 and the motor unit 4, the operator returns the engagement/disengagement buttons 34 formed on both side surfaces of the motor unit 4.

As the engagement/disengagement buttons 34 are returned, the motor clutch portion 15 is moved in the direction away from the endoscope clutch portion 16. As a result, the motor clutch portion 15 and the endoscope clutch portion 16 are disengaged. Thereafter, the operator moves the integrally combined tube insertion connector 56 and the insertion engagement portion 3D5 upward in the drawing. The insertion engagement portion 3D5 and the tube insertion connector 56 are detached from the storage portion 4A2 of the motor unit 4.

The tube insertion connector 56 which forms the separative conduit 55 is detached from the insertion engagement portion 3D5 in the reverse order of the aforementioned assembly procedure. The operation for separating the endoscope 2, thus, is completed. Thus, the present embodiment is able to provide the same functions and effects of those obtained in Embodiment 2.

It is to be clearly understood that the present invention is not limited to the embodiments as described above, but may be modified into various forms without departing from the scope of the present invention.

What is claimed is:

1. A power driven bending endoscope device with detachable insertion portion comprising:
   an insertion body including a thin and long flexible tube portion which is allowed to be inserted into a subject, a bending portion which is provided on a distal end side of the flexible tube portion and allowed to be bent, a distal rigid portion containing an image pickup device on a distal end side of the bending portion, and an insertion engagement portion; and
   a detachable bending operation unit from/with which the insertion engagement portion of the insertion body is separated/coupled via attachment/detachment units, the detachable bending operation unit containing a bending drive unit for bending the bending portion by pulling and loosening an angle wire provided in the insertion body,
   wherein the insertion engagement portion of the insertion body includes a pulling unit which pulls and loosens the angle wire for bending the bending portion and a bending state detection unit for detecting a bending angle indicating a bending state of the bending portion based on a rotating amount of the pulling unit, and the insertion engagement portion further includes an output unit for outputting a detection result of the bending state detection unit as an electric signal and a first power transmission portion for transmitting a power of the bending drive unit to the pulling unit in an attachment/detachment unit to/from the bending operation unit, the first power transmission portion constituting a detachable engagement unit, and
   wherein the bending operation unit includes an input unit which is electrically connected to the output unit and to which the electric signal outputted from the output unit is inputted in a coupled state and a second driving power transmitting portion for transmitting the power of the bending drive unit to the pulling unit via the first driving power transmission portion in the coupled state in an attachment/detachment unit to/from the insertion body the second driving power transmitting portion constituting the engagement unit, and the bending operation unit further includes therein a control unit which starts a rotation control of the bending drive unit based on the electric signal which is indicative of the bending angle of the bending portion when the bending operation unit and the insertion body are brought into the coupled state from a state where the bending operation unit and the insertion body are separated from each other the electric signal being inputted through the input unit, and which performs the rotation control of the bending drive unit based on the electric signal inputted via the input unit while the bending operation unit is coupled with the insertion body.

2. A power driven bending endoscope device with detachable insertion portion according to claim 1, wherein:
   the bending operation unit further includes a drive state detection unit for detecting a drive state of the bending drive unit to output an electric signal as a detection result to the control unit; and
   the control unit controls the bending drive unit based on the electric signal outputted from the drive state detection unit and the electric signal outputted from the output unit.

3. A power driven bending endoscope device with detachable insertion portion according to claim 1, wherein the attachment/detachment unit includes the output unit, the input unit and an engagement unit for transmitting power generated by the bending drive unit to the bending portion,
   wherein the insertion body and the bending operation unit are coupled to be united and the output unit and the input unit are connected with each other by completion of an engagement of the engagement unit.

4. A power driven bending endoscope device with detachable insertion portion according to claim 3, wherein:
   the engagement unit includes a first power transmission portion for transmitting the power generated by the bending drive unit, and a second power transmission portion to which the power transmitted by the first power transmission portion is transmitted; and
   the first power transmission portion and the second power transmission portion include engagement portions to be engaged at an arbitrary position.

5. A power driven bending endoscope device with detachable insertion portion according to claim 1, wherein the bending state detection unit is a potentiometer for detecting a displacement of a pulling unit associated with an electric motor as the bending drive unit via the engagement unit.

6. A power driven bending endoscope device with detachable insertion portion according to claim 1, wherein the bending state detection unit is a potentiometer for detecting a displacement of a pulling unit associated with an electric motor as the bending drive unit via the engagement unit.

7. A power driven bending endoscope device with detachable insertion portion according to claim 1, further comprising a separative conduit portion detachable with respect to the insertion body, wherein the separative conduit portion includes a tube insertion connector equipped with a port connected to a communication portion communicated with fluid conduit inserted into the insertion body, and a fluid tube corresponding to the fluid conduit provided in communication with the tube insertion connector.

8. A power driven bending endoscope device with detachable insertion portion according to claim 1, further comprising a separative conduit portion detachable with respect to the insertion body, wherein the separative conduit portion includes a tube insertion connector equipped with a port connected to a communication portion communicated with fluid conduit inserted into the insertion body, and a fluid tube corresponding to the fluid conduit provided in communication with the tube insertion connector.

* * * * *